(12) United States Patent
Kushmaro et al.

(10) Patent No.: US 11,096,925 B2
(45) Date of Patent: Aug. 24, 2021

(54) INDOLE DERIVATIVES FOR BIOFILM DISRUPTION AND INHIBITION

(71) Applicant: LIFE MATTERS LTD., Hazav (IL)

(72) Inventors: Ariel Kushmaro, Beer Yaacov (IL); Robert S. Marks, Omer (IL); Karina Golberg, Beer Sheva (IL)

(73) Assignee: Life Matters Ltd., Hazav (IL)

( * ) Notice: Subject to any disclaimer, the term of this patent is extended or adjusted under 35 U.S.C. 154(b) by 0 days.

(21) Appl. No.: 15/862,040

(22) Filed: Jan. 4, 2018

(65) Prior Publication Data

US 2018/0193310 A1 Jul. 12, 2018

Related U.S. Application Data

(63) Continuation-in-part of application No. PCT/IL2016/050732, filed on Jul. 7, 2016.

(30) Foreign Application Priority Data

Jul. 7, 2015 (SG) .............................. 10201505353S

(51) Int. Cl.

| A61K 31/404 | (2006.01) |
|---|---|
| A61K 45/06 | (2006.01) |
| A61P 31/04 | (2006.01) |
| A61L 31/08 | (2006.01) |
| A61L 31/16 | (2006.01) |
| A61L 29/08 | (2006.01) |
| A61L 29/16 | (2006.01) |
| A01N 43/38 | (2006.01) |
| A61K 31/7036 | (2006.01) |

(52) U.S. Cl.
CPC ............ *A61K 31/404* (2013.01); *A01N 43/38* (2013.01); *A61K 31/7036* (2013.01); *A61K 45/06* (2013.01); *A61L 29/08* (2013.01); *A61L 29/16* (2013.01); *A61L 31/08* (2013.01); *A61L 31/16* (2013.01); *A61P 31/04* (2018.01); *A61L 2300/204* (2013.01); *A61L 2300/404* (2013.01)

(58) Field of Classification Search
CPC .................................................. A61K 31/404
See application file for complete search history.

(56) References Cited

U.S. PATENT DOCUMENTS

| 8,278,341 B2 * | 10/2012 | Jong .................... A61K 31/497 514/410 |
|---|---|---|
| 2006/0100264 A1 | 5/2006 | Bjeldanes et al. |
| 2006/0264497 A1 * | 11/2006 | Zeligs .................... A61K 8/492 514/414 |
| 2010/0069355 A1 | 3/2010 | Jong et al. |
| 2016/0037773 A1 | 2/2016 | Qian |

FOREIGN PATENT DOCUMENTS

| JP | 9-110831 A | 4/1997 |
|---|---|---|
| WO | 2005016339 A1 | 2/2005 |
| WO | 2012130698 A1 | 10/2012 |

OTHER PUBLICATIONS

J.R. Gurenlian. The Role of Dental Plaque Biofilm in Oral Health. Journal of Dental Hygiene, vol. 81, No. 5, Oct. 2007, 1-11. (Year: 2007).*
G. Berube. Natural and Synthetic Biologically Active Dimeric Molecules: Anticancer Agents, Anti-HIV Agents, Steroid Derivatives and Opioid Antagonists. Current Medicinal Chemistry, 2006, 13, 131-154. (Year: 2006).*
R. M. Kluge, et al. Comparative Activity of Tobramycin, Amikacin, and Gentamicin Alone and with Carbenicillin Against Pseudomnas aeruginosa. Antimicrobial Agents and Chemotherapy, Oct. 1974, p. 442-446. (Year: 1974).*
Oral-B. "What is Gingivitis," downloaded Dec. 20, 2019 from https://oralb.com/en-us/oral-health/conditions/gums/gingivitis-symptoms-causes-treatments; available on the internet Jan. 6, 2011. (Year: 2011).*
Wikipedia article on "Gingivitis," downloaded Sep. 3, 2020 from https://en.wikipedia.org/wiki/Gingivitis. (Year: 2020).*
Wu, Yao-Hua, et al. Diuretics. 1. 1-Imidoyl-2-(2-and 3-indolyl) indolines. Journal of medicinal chemistry vol. 15, No. 5, pp. 529-534. (1972).
Zhang, Lijun, et al. Fast Synthesis of Hydrazine and Azo Derivatives by Oxidation of Rare-Earth-Metal? Nitrogen Bonds. Organometallics vol. 30, No. 3, pp. 375-378. (2011).
Aires, A. et al. The antimicrobial effects of glucosinolates and their respective enzymatic hydrolysis products on bacteria isolated from the human intestinal tract. Journal of Applied Microbiology, vol. 106, No. 6, pp. 2086-2095. (2009).
Roy, S. et al. Synthesis and antibacterial evaluation of 3, 3?-diindolylmethane derivatives. Medicinal Chemistry Research, vol. 23 No. 3, pp. 1371-1377.(2014).
Uesugi Y. et al. 3-Indolylacetic acid-dependent antibacterial activity in rice plant. Annals of the Phytopathological Society of Japan, vol. 50, pp. 69-71. (1984).
Lee J. H. et al. 7-fluoroindole as an antivirulence compound against Pseudomonas aeruginosa. FEMS microbiology letters, vol. 329, pp. 36-44. (2012).
Brenda V Bertinetti, M Alejandra Rodriguez, Alicia M Godeas and Gabriela M Cabrera. 1H,1'H-[3,3']biindolyl from the terrestrial fungus *Glioclaudium catenulatum*. The Journal of Antibiotics 63, pp. 681-683. (2010).
Wu H, Claus Moser, Heng-Zhuang Wang, Niels Høiby and Zhi-Jun Song. "Strategies for combating bacterial biofilm infections". International Journal of Oral Science 7, pp. 1-7. (2014).
Somei M; Hayashi, H.; Ohmoto, S. "Reduction of indigo: Simple syntheses of 3-acetoxy-, 1-acetyl-2.3-dihydro-, 3-acetoxy-3'-acetyl-, 3-acetoxy-1,3'-diacetyl-2,2'-bisindoles, and 2,2'-bisindole", Heterocycles 44(1), pp. 169-176. (1997).

(Continued)

*Primary Examiner* — Michael P Cohen
(74) *Attorney, Agent, or Firm* — Knobbe, Martens, Olson & Bear LLP

(57) ABSTRACT

A method for inhibiting biofilm formation by bacteria on a surface or disrupting existing biofilm on a surface, including contacting the surface or existing biofilm with 2-(indolin-2-yl)-1H-ind, di(1H-indol-3-yl)methane and 1,1'-biindole, or any combination thereof.

20 Claims, 7 Drawing Sheets

(56) References Cited

OTHER PUBLICATIONS

Bonaventura et al; "Biofilm Formation by Stenotrophomonas maltophilia: Modulation by Quinolones, Trimethoprim-Sulfamethoxazole, and Ceftazidime" Antimicrobial Agents and Chemotherapy, p. 151-160. (2004).
Crossman et al; "Biofilm formation and dispersal in Xanthomonas campestris" Microbes Infect. 6(6):pp. 623-629. (2014).
Ioannidis et al; "Detection of Biofilm Production of Yersinia enterocolitica Strains Isolated from Infected Children and Comparative Antimicrobial Susceptibility of Biofilm Versus Planktonic Forms" Mol Diagn Ther. 18(3):pp. 309-314. (2014).
Lee et al; "3-indolylacetonitrile decreases *Escherichia coli* O157:H7 biofilm formation and Pseudomonas aeruginosa virulence". Environ Microbiol. 13(1):pp. 62-73. (2011).
Lister et al; "*Staphylococcus aureus* biofilms: recent developments in biofilm dispersal" Front Cell Infect Microbiol pp. 1-9 (2014).
International Preliminary Report on Patentability received in PCT Application No. PCT/IL2016/050732, dated Jan. 9, 2018.
Written Opinion received in PCT Application No. PCT/IL2016/050732, dated Sep. 21, 2016.
Cardoso, Elsa Maria, et al. "Chronic periodontitis, inflammatory cytokines, and interrelationship with other chronic diseases." *Postgraduate medicine* 130.1 (2018): 98-104.
Hajishengallis, George. "Periodontitis: from microbial immune subversion to systemic inflammation." *Nature Reviews Immunology* 15.1 (2015): 30.
Kim, Soo-Kyoung, et al., "Anthranilate Deteriorates the Structure of *Pseudomonas aeruginosa* Biofilms and Antagonizes the Biofilm-Enhancing Indole Effect," *Appl. Environ. Microbiol.* 81.7 (2015): 2328-2338.
Lee, Jin-Hyung, et al., "Indole as an intercellular signal in microbial communities," *FEMS microbiology reviews* 34 (2010) 426-444.
Lee, Jin-Hyung, et al., "Roles of indole as an interspecies and interkingdom signaling molecule." *Trends in microbiology* 23.11 (2015): 707-718.
Haque et al; "Quorum sensing pathways in Gram-positive and -negative bacteria: potential of their interruption in abating drug resistance" Journal of Chemotherapy vol. 31 No. 4 pp. 161-187. (2019).
Mai-Prochnow et al; "Gram positive and Gram negative bacteria differ in their sensitivity to cold plasma" Scientific Reports (2016).
Papaenfort et al; "Quorum-Sensing Signal-Response Systems in Gram-Negative Bacteria" Nat Rev Microbiol. (2017).
Stewart "Mechanisms of antibiotic resistance in bacterial biofilms" Int. J. Med. Microbiol. 292, pp. 107-113.(2002).
Chemical Book entry for 2-(Indolin-2-yl)-1H-indole downloaded on Dec. 24, 2020, https://www.chemicalbook.com/ProductChemicalPropertiesCB63052516_EN.htm.

\* cited by examiner

US 11,096,925 B2

INDOLE DERIVATIVES FOR BIOFILM DISRUPTION AND INHIBITION

CROSS-REFERENCE TO RELATED APPLICATIONS

The present application is a Continuation-in-Part of International Application No. PCT/IL2016/050732 filed Jul. 7, 2016, designating the United States, which claims priority to Singapore Patent Application No. 10201505353S, filed Jul. 7, 2015, the entire contents of which are hereby incorporated herein by reference.

TECHNICAL FIELD

The present invention relates in general to prevention of biofilm formation and disruption of existing biofilm.

BACKGROUND

In general, bacteria may exist as single, independent cells (planktonic) or they may be organized into sessile aggregates. The latter form is commonly referred to as the biofilm growth phenotype. Acute infections often involve planktonic bacteria, which are generally treatable with antibiotics, whereas infections involving biofilm-residing bacteria often turn out to be untreatable and will develop into a chronic state. It has been estimated that most bacterial infections in humans are correlated with biofilm and about 50% of the nosocomial infections are indwelling devices-associated.

The ability of many bacteria to adhere to surfaces and to form biofilms has also major implications in a variety of industries including shipping, energy, water, food (e.g. dairy, fish, poultry, meat, and Ready-To-Eat food processing), oil drilling, paper production, marine aquaculture, etc.

Existing methods rely primarily on coating devises and submerged surfaces with a protecting coat, and there is no satisfactory method available for treating medically important biofilm. There is thus a pressing need for novel methods for preventing biofilm formation and disrupting existing biofilm in medical and environmental settings.

SUMMARY

In one aspect, the present invention provides a compound selected from 2-(indolin-2-yl)-1H-indole (compound of formula I), di(1H-indol-3-yl)methane (compound of formula II) and 1,1'-biindole (compound of formula III), or a combination thereof, for use in inhibiting biofilm formation by bacteria on a surface or disrupting existing biofilm on a surface.

In another aspect, the present invention is directed to a compound selected from a compound of formula (I), (II) and (III), or any combination thereof, for use in reducing bacterial virulence.

In a further aspect, the present invention provides a composition comprising a compound selected from a compound of formula (I), (II) and (III), or any combination thereof.

In an additional aspect, the present invention provides a method for inhibiting biofilm formation by bacteria on a surface or disrupting existing biofilm on a surface, comprising contacting said surface or existing biofilm with a compound selected from a compound of formula (I), (II) and (III), or any combination thereof.

In yet another aspect, the present invention is directed to a medical device coated, washed or rinsed with a compound selected from a compound of formula (I), (II) and (III), or any combination thereof.

DETAILED DESCRIPTION OF THE PREFERRED EMBODIMENTS

Figure 1A:
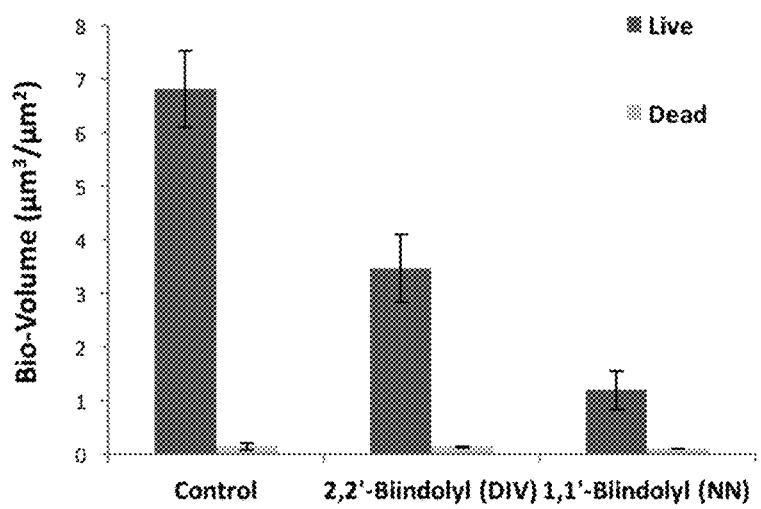
FIGS. 1A-B show prevention of biofilm formation. Confocal laser scanning micrographs (CLSM) of *P. aeruginosa* PA01 (A) and *A. baumannii* (B) formed in glass-bottomed 96 well plates after 18 h of static incubation at 37° C. Cultures were grown in the presence of either 50 µM DIV or NN, or an equivalent amount of DMSO for control. Biofilms were stained using the Live/Dead bacterial viability kit. Live, dead and total bio-volumes ($\mu m^3/\mu m^2$) were calculated based on image analysis and data from the IMARIS software. Bars indicate standard deviations for triplicate sets of experiments.

A structured consortium attached on a living or inert surface formed by microbial cells and surrounded by the self-produced extracellular polymeric matrix is known as biofilm. Biofilms are thus defined as microbially derived sessile communities characterized by cells that are irreversibly attached to a substratum or interface or to each other, are embedded in a matrix of extracellular polymeric substances that they have produced, and exhibit an altered phenotype with respect to growth rate and gene transcription. A typical development of biofilm—taking *Pseudomonas aeruginosa* as an example—includes several stages, i.e., attachment to a surface; formation of microcolonies; development of young biofilm; differentiation of structured mature biofilm, and dispersal of mature biofilm. Pathogenic bacteria residing in biofilms can cause chronic infections, and aggressive and intensive antibiotic treatment is usually helpful to control the exacerbations of such infections induced by dispersed bacteria and reduce the biofilms, but cannot eradicate the biofilm infections, because the minimal concentration of antibiotic for eradication of mature biofilm is difficult to reach in vivo. Therefore, once a bacterial biofilm infection is established, it becomes difficult to eradicate. Bacterial biofilm formation is widely found in natural environments with water, and also in human diseases, especially in patients with indwelling devices for the purpose of medical treatments (Wu et al., 2014).

The inventors of the present invention have screened over 100 bacterial isolates obtained from several coral species for their anti-biofilm activity and abilities to inhibit quorum sensing (QS) using different bioreporter strains. The present invention is based on the finding that two compounds identified in the screen as 1,1'-Biindole (hereinafter, "NN") (CAS Registry Number 479500-92-0) 2-(indolin-2-yl)-1H-indole (hereinafter, "DIV") (CAS Registry Number 38505-89-4) were found to inhibit biofilm formation, attenuate bacterial virulence and disassemble or reduce existing biofilm. NN was first prepared and characterized by Zhang et al. (2011). DIV was first prepared and characterized by Somei et al., (1997). In addition, it was found that the anti-cancer compound di(1H-indol-3-yl)methane (hereinafter, "DIM") (CAS Registry Number 1968-05-4; WO 98/50357) has similar properties. DIM has further been shown to have antibiotic activity against *P. larvae* as determined by agar diffusion method (Brenda et al., 2010), to have antifouling activity (US 2016/0037773), to be an immune response activator (US 2006/0100264) and to be useful for the prevention and or treatment of neurological conditions (WO 2005/016339).

In view of the above, in one aspect, the present invention provides a compound selected from 2-(indolin-2-yl)-1H-indole, di(1H-indol-3-yl)methane and 1,1'-biindole, or a combination thereof, for use in inhibiting biofilm formation by bacteria on a surface or disrupting existing biofilm on a surface.

TABLE 1

Structures I, II and III

Compound of formula I

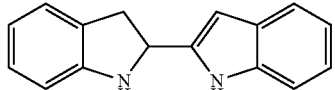

2-(indolin-2-yl)-1H-indole
(DIV)

Compound of formula II

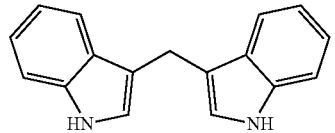

di(1H-indol-3-yl)methane
(DIM)

Compound of formula III

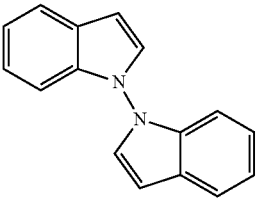

1,1'-Biindole
(NN)

The terms "disrupting", "disassembling", "reducing" and "eradicating" are used interchangeably herein to describe disappearance of an existing biofilm at a rate that is greater than an untreated biofilm or a biofilm treated with a compound known to have no effect on biofilm stability.

In another aspect, the present invention is directed to a method for inhibiting biofilm formation by bacteria on a surface or disrupting existing biofilm on a surface, comprising contacting said surface or existing biofilm with a compound selected from a compound of formula (I), (II) and (III), or any combination thereof.

In certain embodiments, the surface is a surface of a mammalian, poultry or fish cell, tissue or structure. For example, the cell or tissue may be lung, muscle or skin cell or tissue, and the structure is a tooth.

In certain embodiments, the compounds are for use in prophylaxis, metaphylaxis or therapy of an infectious disease caused by bacteria present in biofilm adherent to said cell, tissue or structure surface resulting from said inhibiting biofilm formation or disrupting existing biofilm, and wherein said bacteria is not *Paenibacillus larvae*.

In certain embodiments, the surface is a surface of a medical device intended for insertion into a subject's body, i.e. the compounds and the methods of the present invention may be used in inhibiting biofilm formation by bacteria on a surface of a medical device intended for insertion into a subject's body or disrupting existing biofilm on a surface of a medical device intended for insertion into a subject's body.

In still an additional aspect, the present invention is directed to a medical device intended for insertion into a subject's body, wherein said medical device is coated with a compound selected from a compound of formula (I), (II) and (III), or any combination thereof.

The term "medical devise intended for insertion into a subject's body" as used herein refers to a surgically invasive devices or implantable devices as defined, e.g. but not limited to the European Commission DG Health and Consumer Directorate B, Unit B2 "Cosmetics and medical devices" Guidelines Relating to the Application of the Council Directive 93/42/EEC on Medical Devices.

In certain embodiments, the medical devise intended for insertion into a subject's body is a surgically invasive devices intended for short-term use (>60 minutes,<30 days), such as, but not limited to, clamps, infusion cannulae, skin closure devices, temporary filling materials, tissue stabilisers used in cardiac surgery, cardiovascular catheters, cardiac output probes, temporary pacemaker leads, thoracic catheters intended to drain the heart, including the pericardium, carotid artery shunts, ablation catheter, neurological catheters, cortical electrodes or brachytherapy devices.

In certain embodiments, the medical devise intended for insertion into a subject's body is an implantable device or long-term surgically invasive device (>30 days), such as prosthetic joint replacements, ligaments, shunts, stents and valves (e.g. pulmonary), nails and plates, intra-ocular lenses, internal closure devices (including vascular closure devices), tissue augmentation implants, peripheral vascular catheters, peripheral vascular grafts and stents, penile implants, non-absorbable sutures, bone cements and maxillo-facial implants, visco-elastic surgical devices intended specifically for ophthalmic anterior segment surgery, bridges and crowns, dental filling materials and pins, dental alloys, ceramics and polymers, prosthetic heart valves, aneurysm clips, vascular prosthesis and stents, central vascular catheters, spinal stents, CNS electrodes, cardiovascular sutures, permanent and retrievable vena cava filters, septal occlusion devices, intra-aortic balloon pumps, external left ventricular assisting devices In particular, the surface is a surface of a pacemaker, pacemaker leads, catheter or stent.

The ability of many bacteria to adhere to surfaces and to form biofilms has also major implications in a variety of industries including shipping, energy, water, food (e.g. dairy, fish, poultry, meat, and Ready-To-Eat food processing), oil drilling, paper production, marine aquaculture, etc.

In the case of the food processing industry, biofilm causes chronic bacterial contamination in food processing equipment such as pasteurization pipes and tubes.

In the case of marine-based industries, marine fouling is typically described as comprising several stages, with the early step of bacterial adhesion initiating the formation of a biofilm, which is then followed by secondary colonizers of spores of macroalgae (e.g. enteromorpha intestinalis, ulothrix) and protozoans (e.g. vorticella, *Zoothamnium* sp.) that attach themselves. Lastly, tertiary colonizers—the macrofoulers attach including tunicates, mollusks and sessile Cnidarians. Thus, biofilm formation provides a substratum for biofouling of submerged surfaces such as ship hulls, boat propellers, cages, underwater dock structures, underwater structures on offshore oil platforms, submarine mines, buoys, submarine cables, cooling systems of power plants, pipes and filters of desalination plants etc.

In view of the above, in certain embodiments, the compounds described above may be for use in inhibiting biofilm formation by bacteria on a surface intended for contact with water or an aqueous solution (e.g. milk or any other liquid food processed in the food industry), such as a the surface of ship hulls, boat propellers, cages, underwater dock structures, underwater structures on offshore oil platforms, submarine mines, buoys, submarine cables, cooling systems of power plants, pipes, filters, strains or pumps; i.e. the method of the present invention may be employed in inhibiting biofilm formation by bacteria on a surface of a submerged object or disrupting existing biofilm on such a surface of a submerged object.

The aerial tissues of plants are colonized by a wide variety of bacteria, fungi, and yeasts. These colonizing microorganisms are known as epiphytes. Bacteria are the primary colonizers of leaf surfaces, some of which are spoilage bacteria and some of which are pathogenic bacteria, such as *Campylobacter jejuni, E. coli* 0157:H7, *Salmonella* spp., *Shigella* spp. *Listeria monocyrogenes, Clostridium botulinum, Campylobacter*, and *Bacillus cereus*. These bacteria are also present on other aerial tissues such as flowers and fruits. Furthermore, pathogenic bacteria may adhere to leaves, fruit and vegetables and form biofilm on their surfaces.

It has been found in accordance with the present invention that application of the compound NN and DIM prevents biofilm formation by the bacteria *Erwinia carotovora* known to infect a variety of vegetables and plants including carrots, potatoes, cucumbers, onions, tomatoes, lettuce and ornamental plants like iris (Example 4).

Thus, in certain embodiments, the compounds described above may be for use in inhibiting biofilm formation by bacteria on a surface of a plant cell, tissue or structure.

In certain embodiments the plant may be, but is not limited to, a plant producing carrots, potatoes, cucumbers, onions, tomatoes, lettuce, apples, citrus fruit or plums.

In certain embodiments, the plant cell is derived from and the tissue or structure is selected from a leaf, a root, a flower, a fruit, or other edible structures of a plant.

The biofilm dwelling bacteria subject of the present invention may be any bacteria, i.e. Gram-negative or Gram-positive bacteria or mycoplasmas and spiroplasmas. Within these groups there are bacteria that associate with animal cells, plant cells or artificial surfaces.

In certain embodiments, the bacteria producing and/or residing in the biofilms discussed herein above are Gram-negative bacteria.

The term "Gram-negative bacteria" as used herein refers to bacteria displaying the following characteristics: An inner cell membrane is present (cytoplasmic); A thin peptidoglycan layer is present (This is much thicker in gram-positive bacteria); Has outer membrane containing lipopolysaccharides (LPS, which consists of lipid A, core polysaccharide, and O antigen) in its outer leaflet and phospholipids in the inner leaflet; Porins exist in the outer membrane, which act like pores for particular molecules; Between the outer membrane and the cytoplasmic membrane there is a space filled with a concentrated gel-like substance called periplasm; The S-layer is directly attached to the outer membrane rather than to the peptidoglycan; If present, flagella have four supporting rings instead of two; Teichoic acids or lipoteichoic acids are absent; Lipoproteins are attached to the polysaccharide backbone; Some contain Braun's lipoprotein, which serves as a link between the outer membrane and the peptidoglycan chain by a covalent bond; Most, with very few exceptions, do not form spores.

Examples of Gram-negative bacteria, the biofilms of which can be treated in accordance with the present invention, are, but are not limited to, *Escherichia coli* (*E. coli*), *Salmonella, Shigella*, and other *Enterobacteriaceae, Pseudomonas, Moraxella, Helicobacter, Stenotrophomonas, Bdellovibrio*, acetic acid bacteria, *Legionella* etc. Other notable groups of gram-negative bacteria include the cyanobacteria, spirochaetes, green sulfur, and green non-sulfur bacteria.

Medically relevant gram-negative cocci include the four organisms that cause a sexually transmitted disease (*Neisseria gonorrhoeae*), a meningitis (*Neisseria meningitidis*), and respiratory symptoms (*Moraxella catarrhalis, Haemophilus influenzae*).

Medically relevant gram-negative bacilli include a multitude of species. Some of them cause primarily respiratory problems (*Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*).

Gram-negative bacteria associated with hospital-acquired infections include *Acinetobacter baumannii*, which cause bacteremia, secondary meningitis, and ventilator-associated pneumonia in hospital intensive-care units.

Bacterial adhesion of e.g. the Gram-negative bacteria *vibrio alginolyticus, pseudomonas putrefaciens* or cyanobacteria initiates the formation of biofilm formation as a primary step in marine fouling. [Wikipedia]

Plant pathogenic Gram-negative bacteria are classified within the Phylum *Proteobacteria*. The principal genera of plant Gram-negative pathogenic bacteria are *Agrobacterium, Erwinia, Pseudomonas, Xanthomonas* and *Xylella*. [Plant diseases—Britannica Online Encyclopedia]

In certain embodiments, the Gram-negative bacterial species is selected from *Pseudomonas aeruginosa, Acinetobacter baumannii, Serratia marcescens, Providencia stuartii* and *Erwinia carotovora*.

In certain embodiments, the compounds used in accordance with the present invention are for use in combination with an antibiotic or antibacterial agent. The term "antibiotic" is used interchangeably herein with the term "antibacterial" and refers to a compound that kills or inhibits the growth of bacteria but have no effect on biofilm formation or eradication. Any commercially available antibiotic compound can be used and is chosen by the skilled artisan according to its efficacy against the intended target bacteria.

In certain embodiments, the antibiotic compound is an aminoglycoside, such as Tobramycin, Kanamycin A, Amikacin, Dibekacin, Gentamicin, Sismicin, Netilmicin, Neomycin B, Neomycin C, Neomycin E, Streptomycin and Spectinomycin(Bs); an ansamycin, such as Geldanamycin, Herbimycin and Rifaximin; a carbapenem, such as Imipenem, Meropenem, Ertapenem, Doripenem, Panipenem/betamipron, Biapenem and Tebipenem; a cephalosporin, such as cefaclor, cefprozil and cefuroxime; a glycopeptide, such as Vancomycin, Teicoplanin, Telavancin, Ramoplanin, Dalbavancin, Oritavancin and Decaplanin; a lincosamide, such as Clindamycin and Lincomycin; a lipopeptide, such as Daptomycin; a macrolide, such as Azithromycin, Clarithromycin, Erythromycin, Fidaxomicin, Telithromycin, Carbomycin A, Josamycin, Kitasamycin, Midecamycin/midecamycin acetate, Oleandomycin, Solithromycin, Spiramycin, Troleandomycin, Tylosin/tylocine and Roxithromycin, and a ketolide, such as Telithromycin, Cethromycin and Solthromycin; a monobactam, such as Aztreonam, Tigemonam, Nocardicin A, and Tabtoxin; a nitrofuran, such as Difurazone (also known as Nitrovin), Furazolidone, Nifurfoline, Nifuroxazide, Nifurquinazol, Nifurtoinol, Nifurzide, Nitrofural (also known as nitrofurazone), Nitrofurantoin, Ranbezolid, Furaltadone—an antiprotozoal, Furazidine, Furylfuramide, Nifuratel, and Nifurtimox; an oxazolidinone, such as Linezolid, Posizolid, Tedizolid, Radezolid, Cycloserine, and (S)-5-((isoxazol-3-ylamino)methyl)-3-(2,3,5-trifluoro-4-(4-oxo-3,4-dihydropyridin-1(2H)-yl)phenyl)oxazolidin-2-one; a penicillin, such as Penicillin G, Penicillin K, Penicillin N, Penicillin O, Penicillin V, Methicillin, Nafcillin, Oxacillin, Cloxacillin, Dicloxacillin, Flucloxacillin, Ampicillin, Amoxicillin, Pivampicillin, Hetacillin, Bacampicillin, Metampicillin, Talampicillin, Epicillin, Carbenicillin, Ticarcillin, Temocillin, Mezlocillin, Piperacillin, Clavulanic acid, Sulbactam, and Tazobactam; a polypeptide, such as actinomycin, bacitracin, colistin, and polymyxin B; a fluoro/quinolone, such as Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, and Temafloxacin; a sulfonamid, such as Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole(Co-trimoxazole) (TMP-SMX), and Sulfonamidochrysoidine; a tetracycline, such as Demeclocycline, Doxycycline, Minocycline, Oxytetracycline, and Tetracycline; a DHFR inhibitor, such as Aditoprim, Brodimoprim, Iclaprim, Tetroxoprim, and Trimethoprim; a nitroimidazole, such as Metronidazole, Tinidazole, Nimorazole, Dimetridazole, 6-Amino PA824, Ornidazole, Megazol, Azanidazole, and Benznidazole; Tigecycline; Thiamphenicol; a Quinupristin/Dalfopristin combination; or Mupirocin.

In certain embodiments, the compounds described herein above are used in accordance with the present invention to increase sensitivity of bacteria residing in a biofilm to antibiotic treatment. A statistically significant decrease in the minimally effective concentration of an antibiotic agent required to reduce or eliminate a bacterial infection after treatment of a biofilm with the compound of the present invention as compared with a biofilm-based infection prior to treatment is considered as an increase in sensitivity of bacteria residing in a biofilm to antibiotic treatment.

It has been found in accordance with the present invention that the compounds of formula (I), (II) and (III) suppress prominent virulence determinants (Example 2).

Thus, in an additional aspect, the present invention provides a compound selected from a compound of formula (I), (II) and (III), or any combination thereof, for use in reducing bacterial virulence. Reduction in virulence may be established by measuring a statistically significant reduction in expression or secretion of virulence factors, such as pyocyanin, pyoverdine, elastase (activity of LasB) lipase, rhamnolipids, total protease or chitinase.

In yet an additional aspect, the present invention is directed to a composition comprising a compound selected from a compound of formula (I), (II) and (III), or any combination thereof.

In certain embodiments, the composition further comprises a pharmaceutically acceptable carrier, i.e. it is a pharmaceutical composition.

In certain embodiments the pharmaceutical composition is in the form of a gel, a stick pill, a rinsing liquid, toothpaste, a tablet, a topical medicament, an oral dentifrice, an injectable composition, an oral tablet, a lozenge, a soft gelatin capsule or an aerosol spray.

Methods for coating a surface with a biologically or pharmaceutically active compound are well known in the art. For example, the non-biological surfaces mentioned above, i.e. the surface of a medical device or a surface of a submerged device, may be coated by blending the compounds described above into film-forming components, and are therefore made into an anti-biofilm coating which can be used to inhibit biofilm formation on the surface of the medical device or submerged object. The film-forming components may comprise one or more resin, such as but not limited to, one or more hydrolysable, soluble or insoluble resins. For example, the resins can be one or more of glyptal resin, acrylic resin, chlorinated rubber resin, epoxy resin, silicone resin, polyester resin, polyurethane resin, fluoropolymer resin, and other resins known to those skilled in the art. The film-forming components can be components of paint, such as a marine paint. The anti-biofilm coating may be in the form of paint.

The term "treating" or "therapy" as used herein refers to means of obtaining a desired physiological effect. The effect may be therapeutic in terms of partially or completely curing a disease and/or symptoms attributed to the disease. The term refers to inhibiting the disease, i.e. arresting its development; or ameliorating the disease, i.e. causing regression of the disease.

The term "prophylaxis" as used herein refers to means of preventing or delaying the onset of disease and/or symptoms attributed to the disease.

The term "metaphylaxis" or "metaphylactic" as used herein refers to mass medication of a group of animals, in advance of an expected outbreak of disease.

As used herein, the terms "subject" or "individual" or "animal" or "patient" or "mammal," refers to any subject, particularly a mammalian subject, poultry or fish, for whom diagnosis, prognosis, metaphylactic treatment, prophylactic treatment or therapy is desired, for example, a human or a domesticated mammal such as a pet, farm animal, meat animal, dog, cat, cow, pig, sheep, goat or horse; or poultry and fish.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In certain embodiments, the pharmaceutical composition is adapted for oral administration.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

According to the present invention, any pharmaceutically acceptable salt of the active agent can be used. Examples of pharmaceutically acceptable salts include, without being limited to, the mesylate salt, the esylate salt, the tosylate salt, the sulfate salt, the sulfonate salt, the phosphate salt, the carboxylate salt, the maleate salt, the fumarate salt, the tartrate salt, the benzoate salt, the acetate salt, the hydrochloride salt, and the hydrobromide salt.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

For purposes of clarity, and in no way limiting the scope of the teachings, unless otherwise indicated, all numbers expressing quantities, percentages or proportions, and other numerical values recited herein, should be interpreted as being preceded in all instances by the term "about." Accordingly, the numerical parameters recited in the present specification are approximations that may vary depending on the desired outcome. For example, each numerical parameter may be construed in light of the number of reported significant digits and by applying ordinary rounding techniques.

The invention will now be illustrated by the following non-limiting examples.

EXAMPLES

Materials and Methods 100 bacterial isolates obtained from several coral species were screened for their anti-biofilm activity and abilities to inhibit QS using different bioreporter strains. Active compound identification was performed by separation, reverse thin layer chromatography, followed by preparative HPLC, and finally using MS and NMR spectroscopy. These techniques were used to elucidate the main active structures identified as 1,1'-Biindolyl (NN) and 2-(indolin-2-yl)-1H-indole (DIV) (Table 1).

$^1$H NMR and $^{13}$C NMR spectra and two-dimensional NMR analysis were used to validate the structure and purity of DIV. The chemical shifts were found to be in a good agreement with the results reported by Somei et al. (1997).

$^1$H-NMR (DMSO 400 MHz) δ 3.1 (1H, dd, J=154 and J=9.2 Hz), 3.7 (1H, dd, J=15.4 and 9.2 Hz), 5.8 (1H, dt, J=2.7 and 9.2 Hz), 6.0 (1H, d, J=2.7 Hz), 6.3 (1H, d, J=2.2 Hz), 6.5 (1H, ddd, J=7.3, 6.5, and 1.0 Hz), 6.5 (1H, d, J=7.3 Hz), 6.9 (1H, ddd, J=7.3, 6.5, and 1.0 Hz), 6.9 (1H, t, J=7.3 Hz), 7.0 (1H, ddd, J=7.3, 6.5, and 1.0 Hz), 7.04 (1H, d,J=7.3 Hz), 7.3 (1H, dd, J=7.3 and 1.0 Hz), 7.4 (1H, d, J=7.3 Hz), 11.05 (1H, br s).

$^{13}$C NMR (DMSO 400 MHz): δ 140.0, 130.0, 128.0, 127.8, 125.6, 125.3, 124.5, 122.6, 122.0, 120.0, 118.9, 118.3, 116.7, 111.5, 59.8, 38.0.

EI-MS m/z: 235 (M+H)$^+$.

We have also synthesised DIV to confirm its chemical purity and structural identity. The $^1$H NMR and $^{13}$C NMR spectra of the synthesised DIV were found in a good agreement with the above spectra of the natural DIV compound.

NN was purchased from MolPort, Lacplesa iela 41, Riga, LV-1011, Latvia.

In addition, we tested the commercially available anticancer compound di(1H-indol-3-yl) methane (hereinafter, "DIM") (Table 1), which was purchased from Sigma Aldrich.

Example 1

Biofilm Inhibiting Properties of NN and DIV

Figure 1B:
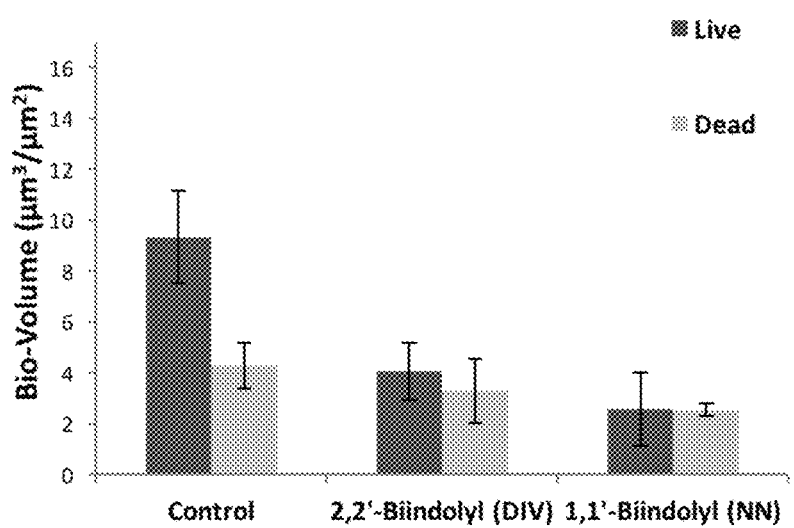

Bioflms of *P. aeruginosa* and *A. baumanii* that were developed on glass slides were determined using confocal scanning laser microscopy (CSLM) (FIG. 1). Accordingly, the density of the biofilms prior to and following treatment by NN and DIV was measured. Both treatments resulted in a reduction of density of attached cells, though NN was the most effective for *P. aureginosa*. DIV and NN treatment showed smaller effects on density of *A. baumanii* model strain. Both treatments resulted in negligible mortality of the bacterial cells as they did not differ from the control.

Figure 2:
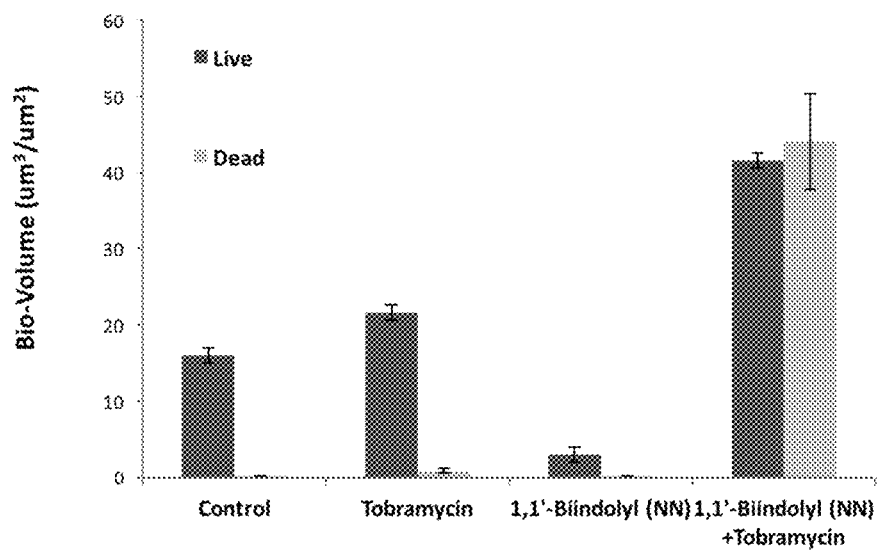
FIG. 2 depicts destruction of *P. aeruginosa* PA01 mature biofilm; biofilm formed in a flow cell after 72 h of incubation at 37° C. and 48 h more in the presence of 50 µM NN, 20 µg/ml Tobramycin, and 50 µM NN with 20 µg/ml tobramycin. Biofilms were stained with Live/Dead bacterial viability kit. Quantification of BioVolume; Live, dead and total bio-volumes ($\mu m^3/\mu m^2$) calculated based on image analysis and data from the IMARIS software. The images were acquired from three different areas in each treatment.

Dynamic growth conditions in flow cell systems are considered to be representative of the real conditions in humeral tissues, where the pathogen thrives in enriched settings. An investigation of the effects of the inhibitor compounds on the bacteria in terms of destruction of already-structured biofilm showed that both compounds had similarly broad anti-biofilm effects on *P. aeruginosa* PA01 mature biofilm (data not shown). Once the efficiency of the new compounds was tested, we proceeded to assess the efficacy of adding antibiotic treatment to the novel compounds to eradicate biofilm (FIG. 2). The *P. aeruginosa* biofilm that had been treated by the antibiotic alone showed little loss of biofilm. When treated by NN alone the biofilm was reduced but not eradicated. On the other hand, when treated by both the antibiotic and the NN, the biofilm was eradicated and the bacterial cells died.

Figure 3A:
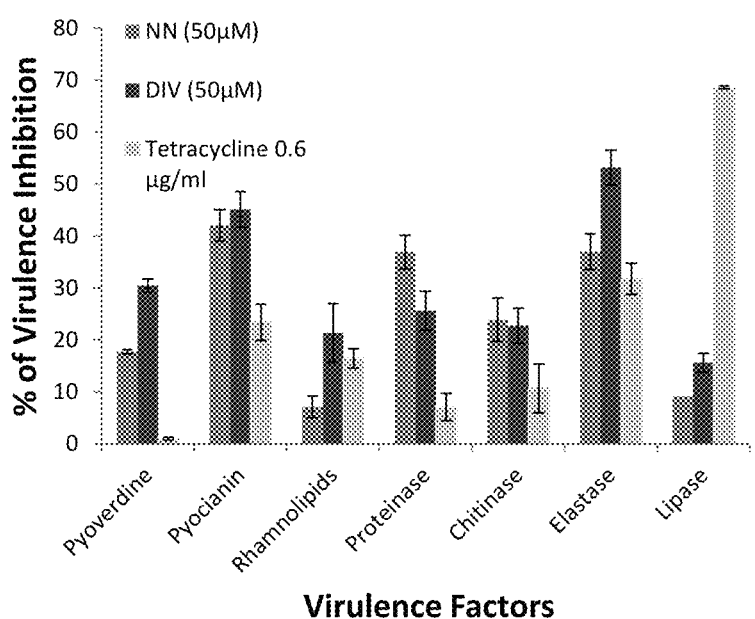
FIGS. 3A-B show effect on, *P. aeruginosa* PA01 pathogenesis. (A) Inhibition of virulence factors production in *P. aeruginosa* PA01, which were grown in the presence of 50 µM NN or DIV. Tetracycline is used as positive control. Results are based on OD measurements distinctive to each factor and normalized to bacterial growth at OD600 nm. Error bars represent SD of three independent repetitions. (B) *C. elegans* killing assay assed by SYTOX Orange stain within 24 h.
Figure 3B:
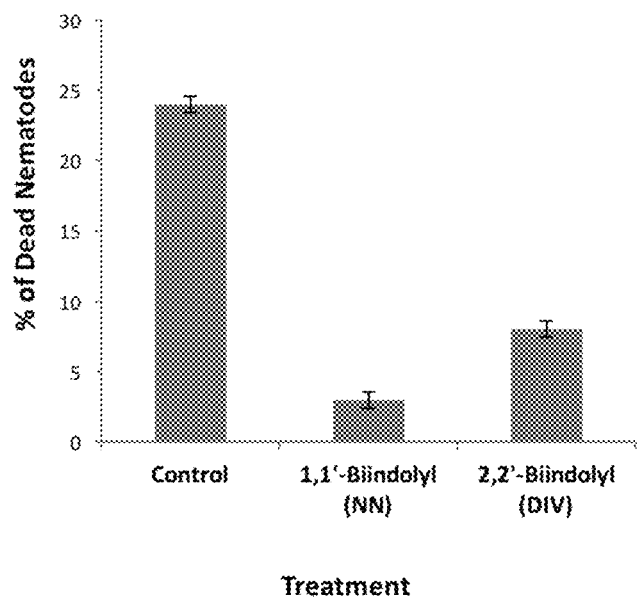

Driven by an arsenal of virulence factors added to the biofilm mode of growth, *P. aeruginosa* PA01 pathogenesis depends on the type of the infection. Therefore, both compounds were tested for their abilities to suppress prominent virulence determinants (FIG. 3A). Quantization of extracellular virulence factors (pyocyanin pyoverdine, elastase (activity of LasB) lipase, rhamnolipids, total protease and chitinase production by *P. aeruginosa* PA01 cell-free culture, was carried out using spectrophotometry. The virulence factors tested, were affected differently by the two compounds. Most of the virulence factors were reduced significantly following exposure of the cells to the two compounds. In addition, we tested NN and DIV on the nematode *Caenorhabditis elegans* infected by *Pseudomonas aeruginosa*. The nematode *C. elegans* is often used as a model for host pathogen interaction in higher multicellular organisms. Measuring nematode survivorship following exposure to *P. aeruginosa* in the absence and presence of modulating compounds, therefore, provides a good model for assessing the effectiveness of the novel compounds on the pathogenesis of the bacteria. In our experiments the improved survivorship of *C. elegans* following exposure to the pathogen in conjunction with our compounds showed that pathogenesis of *P. aeruginosa* is reduced by both of the compounds tested though NN proved to be more effective as it significantly increased survivorship of the nematodes (FIG. 3B).

Figure 4A:
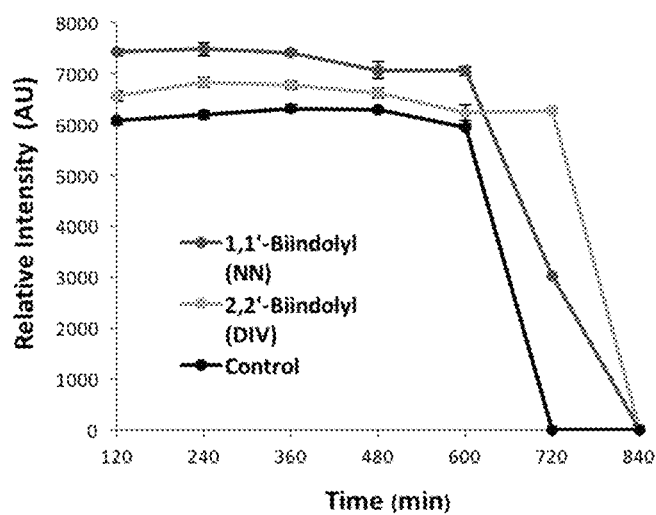
FIGS. 4A-B show reduced adhesion and virulence of *P. aeruginosa* PA01 in human A549 lung cells model. (A) Cytotoxicity effect and apoptosis of A549 cells by *P. aeruginosa* PA01 pre-treated with DIV or NN during 24 h. The infection progress was monitored by calcein staining using Operetta screening system. All the experiments were performed in triplicates. (B) Adhesion of *P. aeruginosa* PA01 ($5 \times 10^7$ CFU/ml) pre-treated with DIV or NN to A549 cells for 1 hr of incubation. Excess bacteria were removed and the released cells were plated followed CFU counts determination.
Figure 4B:
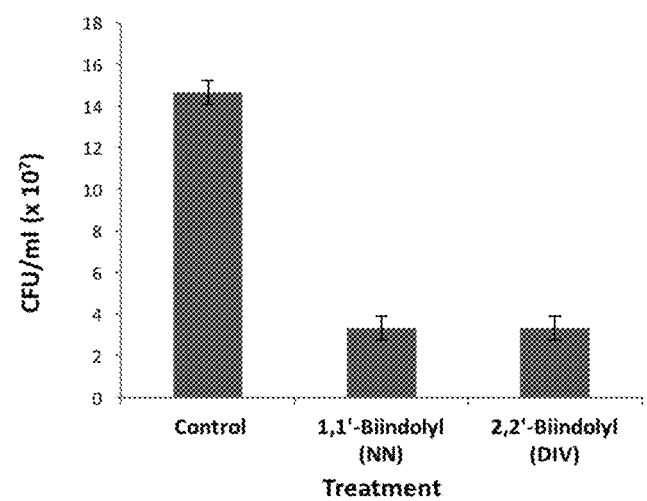
Figure 5A:
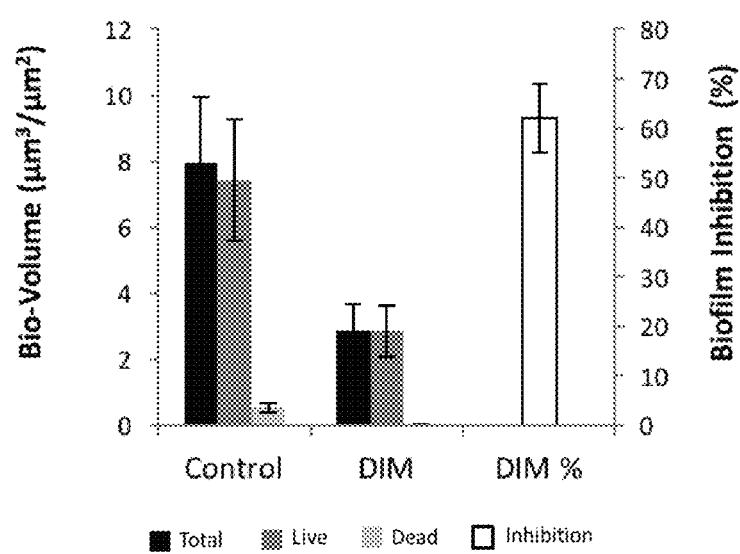
FIGS. 5A-D show biofilm attenuation of the pathogens *P. stuartii* (A), *S. marcescens* (B), *A. baumannii* (C) and *P. aeruginosa* PA01 (D). Cultures were grown in the presence of either 50 µM DIM or an equivalent amount of DMSO for control. Biofilms were stained with the LIVE/DEAD bacterial viability kit. For each species and per treatment, live, dead and total bio-volumes ($\mu m^3/\mu m^2$) were calculated based on image analysis and data from the IMARIS software, and % biofilm inhibition was calculated based on live bio-volumes. The results are the average values of analysis of at least three micrographs.
Figure 5B:
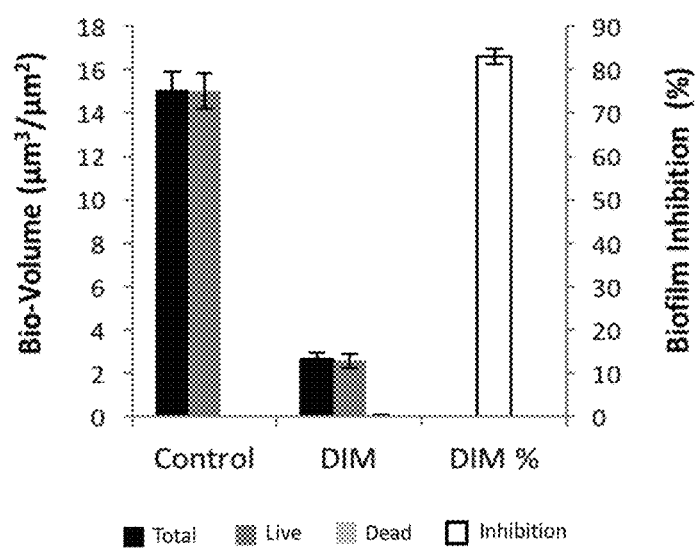
Figure 5C:
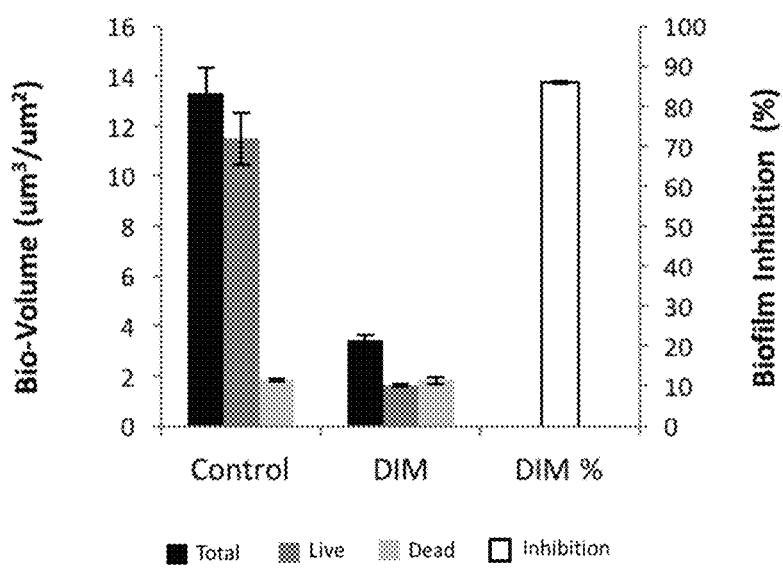
Figure 5D:
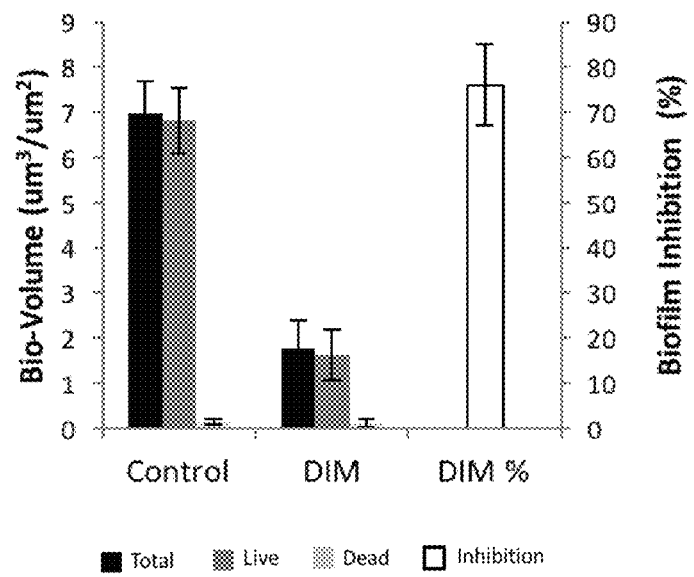

In order to test the possible effects of these compounds on higher organisms, we tested NN and DIV on A549 Human Lung Cell line infected by *P. aeruginosa*. Additional tests were carried out for NN and DIV to assess the effect of this compound to enhance the survival of A549 cells during infection with *P. aeruginosa* PA01. As indicated by greater calcein expression, infection with the pre-treated bacteria suspended the cytotoxicity effect and apoptosis killing in A549 during the incubation (FIG. 4A). Due the fact that adherence to a humeral cell is considered a crucial step in the bacterial infection initiation process, *P. aeruginosa* PA01 pre-treated with DIV or NN was tested for its adherence potency to lung epithelial cells A549. When compared to release following culture of the bacteria in DMSO, culture in either of the compounds (NN or DIV) resulted in similar percentage of release of the pathogenic *P. aeruginosa* PA01 from infected cells cultured in the 96-well plate (FIG. 4B).

Example 2

Biofilm Inhibiting Properties of 3,3'-Diindolylmethane (DIM)

In addition, we tested the anti-biofilm properties of the well-studied anti-cancer compound 3,3'-Diindolylmethane (DIM), a metabolite found in cruciferous vegetables. Inhibition of biofilm establishment by DIM was investigated with different clinical pathogens under static conditions. Biofilm formation by *A. baumannii* and *P. aeruginosa* was further tested in a dynamic flow-cell system, in which biofilm inhibition levels of 86% and 76% were obtained, respectively. Combined treatment comprising tobramycin and DIM showed significant biofilm formation inhibition percentages of 94% that manifested in the almost complete eradication of bacteria. Moreover, the results also suggest that DIM can potentially inhibit the secretion of a distinctive virulence factor by *P. aeruginosa*. Further examination of the hypothesized synergistic effect obtained by combining conventional antibiotics with the DIM compound may offer a promising strategy for the eradication of biofilm complexes.

The current study investigated the influence of DIM on the biofilm formation process and on the destruction of existing biofilms of several pathogenic gram-negative bacterial strains. The introduction of DIM to bacterial cultures led to the formation of substantially reduced biofilms by *A. baumannii, S. marcescens, P. stuartii*, and *P. aeruginosa* PA01 when compared to the thick, live biofilms of the control samples (FIG. 5A-D).

Figure 6:
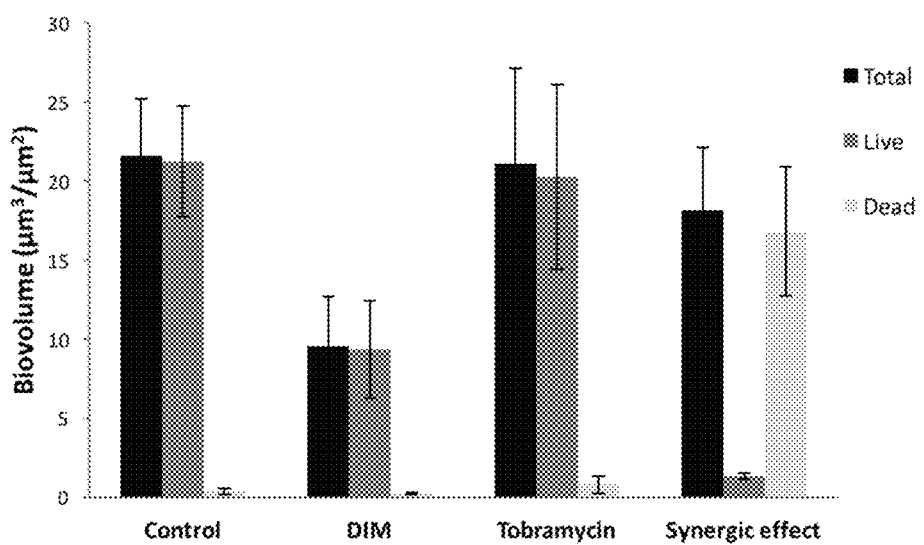
FIG. 6. depicts destruction of mature, differentiated biofilm of *P. aeruginosa* PA01. Statistical analysis of CSLM images of biofilm formed in a flow system after 120 h, and with supplementation of 50 µM DIM, 20 µg/ml Tobramycin and a combined treatment of 50 µM DIM with 20 µg/ml Tobramycin. Biofilms were stained with the LIVE/DEAD bacterial viability kit. Quantification of bio-volume: live, dead and total bio-volumes (μm³/μm²) were calculated based on image analysis and data from the IMARIS software.

To investigate the combined destructive effect of the biofilm inhibitor compound and an antibiotic, *P. aeruginosa* PA01 was cultured for 72 h in the continuous flow system until a mature biofilm had been established Immediately after its establishment, the biofilm was challenged with DIM and/or the antibiotic tobramycin, the known activity of which is protein synthesis inhibition (FIG. 6). Biofilms formation after 48 h showed that addition of only tobramycin resulted in dense biofilm similar to that of the control. In contrast, the addition of DIM alone to the medium supplied to the biofilm cells led to the destruction of existing, stable biofilm—and thus, to a more sparsely distributed architecture—possibly by enhancing detachment of the biofilm from the surface, which resulted in the exposed planktonic bacteria being washed away. In stark contrast, the synergic DIM-tobramycin treatment almost completely eradicated the biofilm, a difference clearly manifested in the number of dead cells.

Figure 7:
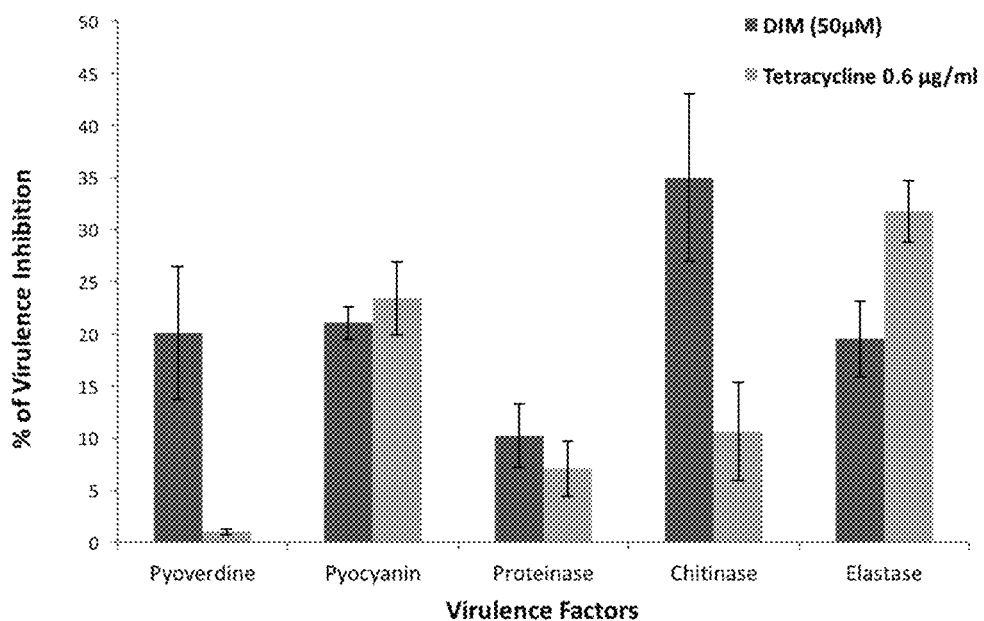
FIG. 7. shows inhibition of virulence factor production in *P. aeruginosa* PA01 that was grown in the presence of 50 μM DIM or 0.6 μg/ml tetracycline treatment as a positive control. Results are based on OD measurements specific to each factor and normalized to the growth OD of 600 nm. Bars indicate standard deviations for triplicate sets of experiments.

DIM exhibits a potential to interfere with the cellular pathways involved in virulence factor production. The basis of *P. aeruginosa* pathogenicity is an arsenal of virulence determinants designed for survival and proliferation in the host that enable bacterial invasion and the subsequent establishment of infection. The success of this microorganism is largely due to its ability to form intractable biofilms and to produce myriad virulence factors controlled by a quorum-sensing (QS) system. A significant reduction of 35% in chitinase production was observed in the presence of 50 µM DIM, while smaller reductions of 20%, 21%, 10% and 19% were observed in pyoverdine, pyocyanin, protease and elastase, respectively (FIG. 7).

Example 3

Biofilm Inhibiting Properties of DIM and NN on Plant-Associated Bacteria

*Erwinia carotovora* was cultured in glass-bottomed 96 well plates for 18 h in static conditions. The growth medium was provided with either 50 µM DIM or NN and the resulted biofilms was investigated using CSLM.

Figure 8:
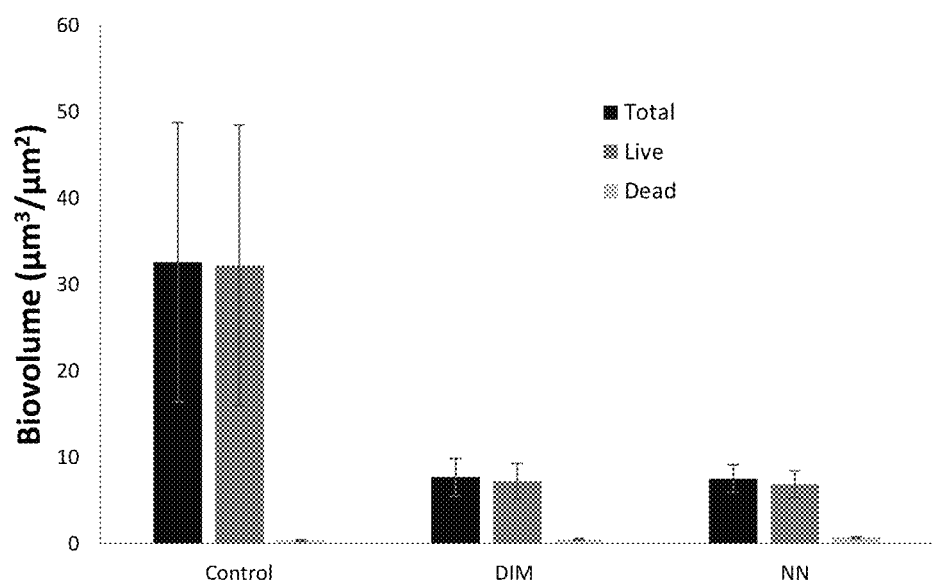
FIG. 8 shows prevention of biofilm formation by *Erwinia carotovora*. Biofilm formed in glass-bottomed 96 well plates after 18 h of static incubation at 37° C. was investigated by confocal laser scanning micrographs (CLSM). Cultures were grown in the presence of either 50 μM DIM or NN, or an equivalent amount of DMSO for control. Biofilms were stained using the Live/Dead bacterial viability kit. Live, dead and total bio-volumes (μm³/μm²) were calculated based on image analysis and data from the IMARIS software.

Both treatments resulted in a significant reduction of density of attached cells (FIG. 8).

REFERENCES

Brenda V Bertinetti, M Alejandra Rodriguez, Alicia M Godeas and Gabriela M Cabrera. 1H,1'H-[3,3']biindolyl from the terrestrial fungus *Gliocladium catenulatum*. The Journal of Antibiotics (2010) 63, 681-683.

Somei M; Hayashi, H.; Ohmoto, S. "*Reduction of indigo: Simple syntheses of 3-acetoxy-, 1-acetyl-2.3-dihydro-, 3-acetoxy-3'-acetyl-, 3-acetoxy-1,3'-diacetyl-2,2'-bisindoles, and 2,2'-bisindole*", Heterocycles 1997, 44(1), pp. 169-176.

Wu H, Claus Moser, Heng-Zhuang Wang, Niels Høiby and Zhi-Jun Song. "*Strategies for combating bacterial biofilm infections*". International Journal of Oral Science (2014) 7, 1-7.

Zhang L, Jing Xia, Qinghai Li, Xihong Li, and Shaowu Wang "*Fast Synthesis of Hydrazine and Azo Derivatives by Oxidation of Rare-Earth-Metal-Nitrogen Bonds*", Organometallics 2011, 30, 375-378.

What is claimed is:

1. A method for inhibiting biofilm formation by Gram-negative bacteria on a surface, comprising:
contacting said surface with an effective amount of a compound selected from the group consisting of 2-(indolin-2-yl)-1H-indole, di(1H-indol-3-yl)methane and 1,1'-biindole, and any combination thereof, thereby inhibiting the biofilm formation by Gram-negative bacteria on the surface.

2. The method of claim 1, wherein said surface is a surface of a mammalian, poultry or fish cell, tissue, or structure.

3. The method of claim 2, for prophylaxis, metaphylaxis or therapy of an infectious disease caused by bacteria present in biofilm adherent to said cell, tissue or structure surface wherein said prophylaxis, metaphylaxis or therapy results from said inhibiting biofilm formation.

4. The method of claim 2, wherein said cell or tissue is lung, muscle or skin cell or tissue, and said structure is a tooth.

5. The method of claim 1, wherein said surface is a surface of a plant cell, tissue, or structure.

6. The method of claim 1, wherein said surface is a surface of a medical device intended for insertion into a subject's body.

7. The method of claim 6, wherein said medical device is a pacemaker, pacemaker lead, catheter, or stent.

8. The method of claim 1, wherein said surface is capable of being contacted with water or an aqueous solution.

9. The method of claim 8, wherein said surface is a surface of a ship hull, a pipe, a filter, a strain or a pump.

10. The method of claim 1, wherein said surface is a surface of a submerged object.

11. The method of claim 10, wherein said surface is a surface of a ship hull, a pipe, a filter, a strain or a pump.

12. The method of claim 1, wherein said Gram-negative bacteria is selected from the group consisting of acetic acid bacteria; *Acinetobacter*;

Bdellovibrio; *Escherichia coli* (*E. coli*), *Salmonella, Shigella*, and other Enterobacteriaceae;

*Erwinia; Haemophilus influenzae; Helicobacter; Klebsiella pneumoniae; Legionella;*

*Moraxella; Neisseria gonorrhoeae; Neisseria meningitidis; Proteus mirabilis; Providencia;*

*Pseudomonas; Serratia; Stenotrophomonas*, and more specifically from *Pseudomonas aeruginosa, Acinetobacter baumannii, Serratia marcescens, Providencia stuartii* and *Erwinia carotovora*.

13. The method of claim 1, further comprising contacting said surface with said compound in combination with an antibacterial agent.

14. The method of claim 1, wherein sensitivity of said bacteria to antibiotic treatment is increased.

15. A method for disrupting an existing biofilm on a surface, comprising:
    contacting said surface or said existing biofilm with an effective amount of a compound selected from the group consisting of 2-(indolin-2-yl)-1H-indole, di(1H-indol-3-yl)methane and 1,1'-biindole, and any combination thereof, and
    disrupting the existing biofilm formed by a gram-negative bacteria on the surface.

16. The method of claim 15, wherein said surface is a surface of a mammalian, poultry or fish cell, tissue or structure.

17. The method of claim 16, for prophylaxis, metaphylaxis or therapy of an infectious disease caused by bacteria present in biofilm adherent to said cell, tissue or structure surface, wherein said prophylaxis, metaphylaxis or therapy results from said disrupting said existing biofilm.

18. The method of claim 17, wherein said cell or tissue is lung, muscle or skin cell or tissue, and said structure is a tooth.

19. The method of claim 15, further comprising contacting said surface or existing biofilm with said compound in combination with an antibacterial agent.

20. The method of claim 15, wherein said surface is a surface of a submerged object.

* * * * *